(12) United States Patent
Deshpande et al.

(10) Patent No.: US 7,141,702 B2
(45) Date of Patent: Nov. 28, 2006

(54) PROCESS FOR THE SYNTHESIS OF α-SUBSTITUTED ACROLEINS

(75) Inventors: Raj M. Deshpande, Pune (IN);
Makarand M. Diwakar, Pune (IN);
Raghunath V. Chaudhari, Pune (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 10/810,463

(22) Filed: Mar. 26, 2004

(65) Prior Publication Data

US 2005/0215829 A1    Sep. 29, 2005

(51) Int. Cl.
*C07C 45/50* (2006.01)
(52) U.S. Cl. .................. 568/454; 568/559; 568/461
(58) Field of Classification Search ............ 568/454, 568/459, 461
See application file for complete search history.

(56) References Cited

U.S. PATENT DOCUMENTS

| | | |
|---|---|---|
| 4,041,082 A | 8/1977 | Onoda et al. |
| 4,408,079 A | 10/1983 | Merger et al. |
| 4,496,770 A * | 1/1985 | Duembgen et al. ......... 568/463 |
| 5,064,508 A | 11/1991 | Weber et al. |
| 5,689,010 A * | 11/1997 | Paciello et al. ............ 568/451 |
| 6,225,507 B1 | 5/2001 | Giessler et al. |

OTHER PUBLICATIONS

R.M. Deshpande et al., "Biphasic catalysis for a selective oxo-Mannich tendem synthesis of methacrolein", Journal of Molecular Catalysis A: chemical 211 (1-2) 49-53 Coden: JMCCF2, 1381-1169, 2004.

* cited by examiner

*Primary Examiner*—Sikarl A. Witherspoon
(74) *Attorney, Agent, or Firm*—Darby & Darby

(57) ABSTRACT

The present invention provides an improved process for the synthesis of α-substituted acroleins from olefins by a tandem hydroformylation and Mannich reaction sequence in the presence of syngas and formaldehyde, wherein the two catalysts are segregated into two different phases thereby preventing deactivation of the catalysts by each other, and yielding a highly selective and active catalyst.

24 Claims, No Drawings

PROCESS FOR THE SYNTHESIS OF α-SUBSTITUTED ACROLEINS

FIELD OF INVENTION

The present invention provides an improved process for the synthesis of α-substituted acroleins of formula $CH_2=CR-CHO$ where R is an alkyl or aryl group.

The present invention particularly provides a single stage synthesis of alpha substituted acroleins from olefins by a tandem hydroformylation and Mannich reaction sequence in the presence of syngas and formaldehyde. The two catalysts employed for the tandem reaction can interact with each other and get deactivated, if present in one phase. These catalysts are hence segregated into two different phases thereby preventing deactivation of the catalysts by each other, and yielding a highly selective and active catalyst.

BACKGROUND OF THE INVENTION

α-substituted acroleins find application in specialty polymers and pharmaceuticals. The sequential hydroformylation—Mannich reaction for the formation of α-β unsaturated aldehydes is very well documented in literature. The reaction proposed invariably deal with the formation of an unsaturated aldehyde by condensation of two aldehyde molecules, both of which are in turn prepared by the hydrofomylation of olefins. In effect the reaction is a hydrofomylation-homoaldol reaction since the aldol reaction is mainly between two similar aldehyde molecules. The hydroformylation of propene followed by the aldol condensation of the formed butyraldehyde as a route to 2 ethyl hexanol is Very well documented and is a commercial application. In this context reference may be made to British Patent 1002429 wherein the preparation of 2 ethyl hexanol via the hydrofomylation of propene is proposed. The catalysts used in this invention relate to cobalt compounds and the reaction is carried out between the butraldehyde formed via the hydroformylation reaction. The reaction is conducted in a basic medium that is a homogeneous phases. The drawbacks are that the aldol condensation is a homoaldol formation and not a hetero-aldol reaction as proposed in the present invention.

Reference is made to U.S. Pat. No. 6,573,414 wherein the formation of $C_9$ and $C_{10}$ alcohols is achieved by a hydroformylation of butene to $C_5$ aldehydes followed by aldol condensation to yield $C_{10}$ alcohols. The drawbacks are that the different reactions involved viz hydroformylation, aldolisation and subsequent hydrogenation are carried out in multiple stage and not in a single reactor as is claimed in the present invention.

Reference is made to U.S. Pat. No. 5,689,010 wherein a single stage process for the hydroformylation and aldol condensation has been proposed. In this patent the aldol condensation is primarily between the aldehydes formed in the course of hydroformylation reaction. Due to such a system it is not possible to achieve a hetero aldol condensation which is necessary to achieve the formation of a substituted acroleins.

A one stage process for the preparation of higher aldehydes by hydroformylation-aldol condensation is described in PCT Application WO 80/01691. Herein rhodium complex catalysts have been proposed for hydroformylation of higher α-olefins. The aldol condensation is catalyzed by the presence of bases like KOH and Lewis bases. Here too only homo aldol formation is carried out.

Reference is made to U.S. Pat. No. 3,278,612 wherein the use of alkaline medium has been postulated to achieve hydroformylation-aldol condensation in the presence of cobalt catalysts. The drawbacks are that this invention pertains to homo aldol condensation.

Reference is also be made to U.S. Pat. Nos. 4,426,542, 5,463,147, 5,462,986, 5,369,162, 5,382,716 and 5,268,514 wherein a multistage process incorporating hydroformylation, followed by aldol condensation of the formed aldehydes with subsequent hydrogenation of the unsaturated aldehydes to higher alcohols is proposed. In all these patents no reference is made to the aldol condensation of two dissimilar aldehydes.

Synthesis of α-substituted acroleins by reaction of aldehydes with formaldehyde in the presence of a base is well documented in literature. [See for reference Ulllmann's Encyclopeida of Industrial Chemistry, Vol A1, page 149 to 160, $5^{th}$ edition] The aldol condensation of propionaldehydes with formaldehyde to yield methacrolein is also a very well practiced process as indicated in the above reference.

Reference is made to U.S. Pat. Nos. 4,408,079 and 4,496,770 wherein aldol condensation of aldehyde and formaldehyde is reported in the presence of secondary amine catalysts to yield α-alkyl acroleins. The use of amines in the presence of organic acids is also said to improve the yield of the desired product. In these patents the aldol condensation is a unique reaction and not coupled with any other previous reaction, which generates the aldehyde. The use of a two-phase system has also not been mentioned.

In all the above mentioned prior art the following drawbacks can be summarized:

(i) Sequential hydroformylation of olefin followed by aldol condensation of the formed aldehyde with formaldehyde already present in the reaction medium, has not been mentioned.
(ii) The deactivation of the aldolisation catalysts in the presence of the hydroformylation catalysts, formaldehyde under reaction conditions has not been indicated.
(iii) The use of a strategy to segregate the two catalysts to achieve the desired synthesis of substituted acroleins has not been mentioned.

OBJECTS OF THE INVENTION

The main object of the present invention is to provide an improved process for the tandem synthesis of α-substituted acroleins having formula (I), which obviates the drawbacks as detailed above.

Another object of the present invention is to provide a strategy for the segregation of two incompatible catalysts into two distinct phases in order to ensure a tandem reaction sequence, such segregation can provide a method for the conversion of multistage processes into a single stage reaction, as has been shown for the preparation of α-substituted acroleins.

Yet another objective of the present invention is to promote the cross aldol reaction between an aldehyde formed by the hydroformylation reaction, and formaldehyde already present in the reaction medium, to achieve the desired preparation of α substituted acrolein in high yield.

SUMMARY OF THE INVENTION

Accordingly the present invention provides a process for the synthesis of a αsubstituted acrolein of the formula $CH_2=CR-CHO$ where R is an alkyl or aryl group, the process comprising i. subjecting a mixture of an olefin and syngas or a mixture of olefin and carbon monoxide and hydrogen to hydroformylation in organic phase and in the presence of a hydroformylation catalyst or catalyst precursor comprising a rhodium complex catalyst or catalyst precursor to obtain the corresponding aldehyde;

ii. subjecting the aldehyde obtained in step (i) above to aldol condensation with formaldehyde in the presence of an aldolisation catalyst comprising secondary amine or a secondary amine/organic acid catalyst in aqueous phase, the reactions of steps (i) and (ii) being carried out simultaneously in a biphasic aqueous-organic system, ensuring the segregation of the two catalysts into two distinct phases, to obtain an α-substituted acrolein.

In one embodiment of the invention, the rhodium complex catalyst comprises an organometallic complex of rhodium of the formula Rh $(A)_p (B)_q (C)_r (D)_s$, wherein A, B, C and D are ligands selected from the group consisting of H, trialkyl phosphines, triaryl phosphines, carbonyl, trialkyl arsine, triaryl arsines, alkyl aryl phosphines, trialkyl amines, triaryl amines, alkyl aryl amines, bisphosphines and diimines and p+q+r+s is equal to 4, 5 or 6, such that the resultant complex is soluble in the organic phase.

In another embodiment of the invention, the organic phase comprises an organic media selected from the group consisting of aromatic hydrocarbons, aliphatic hydrocarbons, higher alcohols and any mixtures thereof.

In a further embodiment of the invention, the rhodium complex catalyst is selected from the group consisting of $HRh(CO)(PPh_3)_3$, $Rh(CO)(Cl)(PPh_3)_2$, $RH(CO)_2$(acetylacetone), $[Rh(Cyclooctadiene)Cl]_2$, $HRh(CO)(Pn\text{-}butyl_3)_3$, $HRh(CO)(PPh_3)$(diphenylphosphinoethane), $HRh(CO)(PPh_3)$(diphenylphosphinopropane) and $HRh(CO)(PPh_3)$(diphenylphosphinbutane).

In another embodiment of the invention, the step of hydroformylation is carried out using a rhodium catalyst precursor with an additional ligand and in the presence of an additional ligand which may or may not be identical to the ligand already coordinated to the rhodium metal precursor.

In yet another embodiment of the invention, the additional ligand is water insoluble and is selected from the group consisting of aryl, alkyl and alkylaryl secondary phosphines, aryl, alkyl and alkylaryl tertiary phosphines, aryl, alkyl and alkylaryl secondary phosphates, aryl, alkyl and alkylaryl tertiary phosphates, aryl, alkyl and alkylaryl secondary arsines, aryl, alkyl and alkylaryl tertiary arsines, aryl, alkyl and alkylaryl tertiary amines, pentanediones, substituted pentanediones, acetylacetonates, Schiff bases and aryl, alkyl and alkylaryl bisphosphines.

In a further embodiment of the invention, the additional ligand is selected from the group consisting of triphenylphosphine, tri n-butylphosphine, acetylacetone, tributylphospite, triphenylphosphite, triphenylamine, tributylamine and triphenylarsine.

In another embodiment of the invention, the reaction is carried out in presence of excess ligand and mole ratio of metal to free ligand is in the range of 0.1 to 10.

In another embodiment of the invention, the aldolisation catalyst is soluble in aqueous medium and comprises a secondary aryl or alkyl amine selected from the group consisting of diethyl amine, dimethyl amine, methyle ethyl amine, dibutly amine, dibenzyl diphenyl amine, piperidine, morpholine, piperazine and pyrolidine.

In another embodiment of the invention the aldolisation reaction is carried out in the presence of an organic acid selected from acetic acid, propionic acid and butyric acid.

In another embodiment of the invention the mole ratio of secondary amine aldolisation catalyst to the organic acid is in the range of 0.01–10.

In another embodiment of the invention the mole ratio of hydroformylation catalyst to the aldolisation catalyst is in the range of 0.01 to 10000, preferably between 0.1 to 1000.

In yet another embodiment of the invention the organic phase of the present invention is immiscible with water and is selected from the group consisting of toluene, xylene, cyclohexane, heptane, decanol and any mixture thereof.

In another embodiment of the invention, formaldehyde is used in the form of an aqueous solution or in the form of paraformaldehyde.

In another embodiment of the invention, the mole ratio of olefin to formaldehyde is in the range of 0.1 to 100, preferably between 0.5 to 10.

In another embodiment of the invention the olefin is selected from substituted and unsubstituted olefins with a carbon number from 2 to 10.

In yet another embodiment of the invention the reaction temperature varies between 20 to 200° C.

In still another embodiment the reaction is conducted in the presence of carbon monoxide and hydrogen, and the pressure of both these varies between 10 to 1500 psi each, and preferably between 50 to 450 psi each.

In yet another embodiment the product α substituted acrolein is preferentially soluble in the organic media.

In still another embodiment the reaction is conducted either as a batch or a continuous reaction with continuous addition of olefin and carbon monoxide and hydrogen dependant on consumption rate thereof.

In still another embodiment the olefin used is ethylene and the product obtained is methacrolein.

DETAILED DESCRIPTION OF THE INVENTION

The present invention provides an improved process for the synthesis of α-substituted acroleins of the formula $CH_2=CR-CHO$ where R is an alkyl or aryl group. The process comprises hydroformylating a mixture of olefin and syngas together or a mixture of olefin and carbon monoxide and hydrogen separately, in presence of a hydrofomylation catalyst or catalyst precursor and in presence or absence of an additional ligand in the organic phase to obtain the corresponding aldehyde. The aldehyde obtained is subjected to aldol condensation with formaldehyde using an aldolisation catalyst in aqueous phase. Both reactions, viz, hydroformylation and aldolisation are conducted simultaneously in a biphasic aqueous-organic system. This ensures the segregation of the two catalysts into two distinct phases, such that the hydroformylation reaction of olefin is catalyzed by a rhodium complex catalyst/precursor and additional ligand, present in the organic medium, and the aldol condensation reaction being catalyzed by an aldolisation catalyst comprising of a secondary amine or a secondary amine/organic acid catalyst present in the aqueous catalyst present in the aqueous medium. The temperature of the reaction is preferably in the range of 25–200° C., and the carbon monoxide and hydrogen pressure in the range of 10–1500 psi.

The rhodium complex catalysts used for the hydroformylation of olefins are organometallic complexes of rhodium having the formula Rh $(A)_p (B)_q (C)_r (D)_s$, where A, B, C, D could be ligands selected from H, trialkyl phosphines, triaryl phosphines, carbonyl, trialkyl arsine, triaryl arsines, alkyl aryl phosphines, tri alkyl amines, triaryl amines, alkyl aryl amines, bisphosphines, diimines and p+q+r+s is equal to 4 or 5 or 6, such that the resultant complex is soluble in the organic media consisting of aromatic hydrocarbons, aliphatic hydrocarbons and higher alcohols or mixtures thereof. Exemplary catalysts that can be used are $HRh(CO)(PPh_3)_3$, $Rh(CO)(Cl)(PPH_3)_2$, $RH(CO)_2$ (acetylacetone), $[Rh (Cyclooctadiene) Cl]_2$, $HRh (CO)(Pn-butyl_3)_3$, (diphenylphosphinoethane), $HRh(CO)(PPh_3)$diphenylphosphinopropane), $HRh(CO)(PPh_3)$(diphenylphosphinbutane), etc.

The reaction is conducted using a rhodium complex precursor, in the presence of additional ligand which may or may not be identical to the ligand already coordinated to the metal precursor, the ligands employed being water insoluble and could belong to the general family aryl, alkyl and alkylaryl secondary or tertiary phosphines; aryl, alkyl and alkylaryl secondary or tertiary phosphates; aryl alkyl and alkylaryl secondary or tertiary arsines; aryl and alkylaryl tertiary amines; pentanediones, and substituted pentanediones, acetylacetonates; Schiff bases; aryl, alkyl and alkylaryl bisphosphines. Exemplary ligands that can be used are triphenylphosphine, tri n-butylphosphine, acetylacetone, tributylphospite, triphenylphosphite, triphenyl amine, tributylamine, triphenylarsine.

The reaction is carried out in presence of excess ligand and mole ratio of metal to free ligand is between 0.1 to 10. The catalyst used for aldol reaction is soluble in aqueous medium and comprises of secondary aryl or alkyl amines such as diethyl amine, dimethyl amine, methyl ethyl amine, dibutyl amine, dibenzyl diphenyl amine, piperidine, morpholine, piperazine, pyrolidine. The reaction is carried out in the presence of an organic acid selected from acetic acid, propionic acid and butyric acid in order to facilitate the aldolisation reaction. The mole ratio of secondary amine aldolisation catalyst to the added organic acid varies between 0.01–10. The mole ratio of the hydroformylation catalyst to the aldolisation catalyst used varies from 0.01 to 10000, and preferably between 0.1 to 1000.

The organic phase of the present invention is immiscible with water and is selected from aromatic hydrocarbons, aliphatic hydrocarbons and higher alcohols such as toluene, xylene cyclohexane, heptane, decanol and mixtures thereof.

The formaldehyde used is either utilized as an aqueous solution or in the form of paraformaldehyde and can comprise commercial available formaldehyde solution that is stabilized.

The formaldehyde is taken in proportion to the amount of olefin, the mole ratio of olefin to formaldehyde varies from 0.1 to 100, and preferably between 0.5 to 10. The ratio of the formaldehyde to the olefin can decide the activity for the aldolisation reaction. The presence of excess of formaldehyde can result in favouring cross aldolisation, which is the desired reaction. The olefin can be a substituted or unsubstituted olefin with a carbon number from 2 to 10. The reaction is conducted in the presence of carbon monoxide and hydrogen, and the pressure of both these varies between 10 to 1500 psi each, and preferably between 50 to 450 psi each.

The product α substituted acrolein is preferentially soluble in the organic medium. The reaction can be conducted either as a batch or a continuous reaction with continuous addition of olefin and carbon monoxide and hydrogen as per the consumption. In one feature of the invention, the olefin used is ethylene and the product obtained is methacrolein.

The process of the present invention is described hereinbelow with reference to the examples, which are illustrative and should not be construed to limit the scope of the present invention in any manner.

Examples 1 and 2 show that in the absence of segregation of the two catalysts the aldolisation catalyst gets deactivated, and no methacrolein is formed.

EXAMPLE 1

A reaction was conducted in a 300 ml Stainless steel reactor as follows:

Aqueous phase—90 cm$^3$ water containing 0.37 mol formaldehyde, diethyl amine—$8.4 \times 10^{-3}$ mol, acetic acid—$8.8 \times 10^{-3}$ mol $(Rh(COD)Cl)_2$ $4.09 \times 10^{-6}$ mol. Rh: Triphenyl phosphine trisulfanotosodium [TPPTS] 1:60; organic phase—10 cm$^3$ toluene. The autoclave was pressurized with syngas 3.772 Mpa, (CO:H$_2$, 1:1) and ethylene 0.419 Mpa. The autoclave was heated up to 333K and the reaction was continued for 6 hours. An induction period of 30 minutes was observed. At the end of the reaction the autoclave and it contents were cooled to room temperature. Analysis of the reaction mixture showed a 0.021 moles propionaldehyde. No methacrolein was formed.

EXAMPLE 2

A reaction was conducted in a 300 ml Stainless steel reactor as follows:

Aqueous phase—90 cm$^3$ water containing 0.37 mol formaldehyde: organic phase—10 cm$^3$ toluene containing diphenyl amine—$8.4 \times 10^{-3}$ mol, $(HRh(CO)(PPh_3)_3$ $4.09 \times 10^{-6}$ mol, Rh: Triphenyl phosphine 1:6. The autoclave was pressurized with syngas 3.772 Mpa, (CO: H$_2$, 1:1) and ethylene 0.419 MPA. The autoclave was heated up to 333 k and the reaction was continued for 6 hours. At the end of the reaction the autoclave and its contents were cooled to room temperature. Analysis of the reaction mixture showed 0.020 moles propionaldehyde. No methacrolein was formed.

The above two examples show that a tandem reaction is not feasible when the hydroformylation and aldolisation catalysts are in the same phase. Only propionaldehyde is formed with no aldol condensation as the aldolisation catalyst is deactivated.

Examples 3 to 7 show the effect of segregation of catalysts to achieve a tandem synthesis of methacrolein, and the use of various secondary amines and organic acids to achieve the tandem reaction.

EXAMPLE 3

A reaction was conducted in a 300 ml Stainless steel reactor as follows:

Aqueous phase—(35%) formaldehyde—30 cm$^3$, water—50 cm$^3$, diethyl amine $8.4 \times 10^{-3}$ moles, acetic acid—$8.8 \times 10^{-3}$ moles; organic phase: Toluene 20 cm$^3$, $HRh(CO)(PPh^3)_3$—$2.72 \times 10^{-5}$ moles, $PPh_3$—$1.83 \times 10^{-4}$ moles. The autoclave was pressurized with syngas 3.772 Mpa, (CO:H$_2$, 1:1) and ethylene 0.419 Mpa. The autoclave was heated up to 333K and the reaction was continued for 6 hours. At the end of the reaction the autoclave and its contents were cooled to room temperature. The analysis of the product showed 67% conversion of ethylene with propionaldehyde 0.00176 mol and methacrolein 0.0187 mol.

EXAMPLE 4

A reaction was conducted in a 300 ml Stainless steel reactor as follows:

Aqueous phase—(35%) formaldehyde—30 cm$^3$, water—50 cm$^3$, morpholine 8.4×10$^{-3}$ moles, acetic acid—8.8×10$^{-3}$ moles; organic phase: Toluene—20 cm$^3$, HRh(CO)(PPh$_3$)$_3$—2.72×10$^{-5}$ moles, PPh$_3$—1.83×10$^{-4}$ moles. The autoclave was pressurized with syngas 3.772 MPa, (CO: H$_2$, 1:1) and ethylene 0.419 Mpa. The autoclave was heated up to 333 K and the reaction was continued for 6 hours. At the end of the reaction the autoclave and its contents were cooled to room temperature. The analysis of the product showed 66% conversion of ethylene with propionaldehyde 0.0075 mol and methacrolein 0.011 mol.

EXAMPLE 5

A reaction was conducted in a 300 ml Stainless steel reactor as follows:

Aqueous phase—(35%) formaldehyde—30 cm$^3$, water—50 cm$^3$ piperidine 8.4×10$^{-3}$ moles, acetic acid—8.8×10$^{-3}$ moles; organic phase: Toluene—20 cm$^3$, HRh(CO)(PPh$_3$)$_3$—2.72×10$^{-5}$ moles, PPh$_3$—1.83×10$^{-4}$ moles. The autoclave was pressurized with syngas 3.772 MPa, (CO:H$_2$, 1:1) and ethylene 0.419 Mpa. The autoclaye was heated up to 333 K and the reaction was continued for 6 hours. At the end of the reaction the autoclave and its contents were cooled to room temperature. The analysis of the product showed 66% conversion of ethylene with propionaldehyde 0.0073 mol and methacrolein 0.0101 mol.

EXAMPLE 6

A reaction was conducted in a 300 ml Stainless steel reactor as follows:

Aqueous phase—(35%) formaldehyde—30 cm$^3$, water—50 cm$^3$ diethyl amine 8.4×10$^{-3}$ moles, propionic acid—8.8×10$^{-3}$ moles; organic phase: Toluene—20 cm$^3$, HRh(CO)(PPh$_3$)$_3$—2.72×10$^{-5}$ moles, PPh$_3$—1.83×10$^{-4}$ moles. The autoclave was pressurized with syngas 3.772 MPa, (CO:H$_2$, 1:1) and ethylene 0.419 Mpa. The autoclave was heated up to 333 K and the reaction was continued for 6 hours. At the end of the reaction the autoclave and its contents were cooled to room temperature. The analysis of the product showed 66% conversion of ethylene with propionaldehyde 0.002 mol and methacrolein 0.015 mol.

EXAMPLE 7

A reaction was conducted in a 300 ml Stainless steel reactor as follows:

Aqueous phase—(35%) formaldehyde—30 cm$^3$, water—50 cm$^3$ diethyl amine 8.4×10$^{-3}$ moles, butyric acid—8.8×10$^{-3}$ moles; organic phase: Toluene—20 cm$^3$, HRh(CO)(PPh$_3$)$_3$—2.72×10$^{-5}$ moles, PPh$_3$ 1.83×10$^4$ moles. The autoclave was pressurized with syngas 3.772 MPa, (CO: H$_2$, 1:1) and ethylene 0.419 Mpa. The autoclave was heated up to 333 K and the reaction was continued for 6 hours. At the end of the reaction the autoclave and its contents were cooled to room temperature. The analysis of the product showed 67% conversion of ethylene with propionaldehyde 0.0046 mol and methacrolein 0.0128 mol.

Example 8 shows the improvement on methacrolein yield by a continuous feed of ethylene and syngas as per the consumption.

EXAMPLE 8

To improve the selectivity to methacrolein and to avoid methacrolein degradation a tandem reaction was conducted in the presence of a continuous feed of ethylene and syngas (CO/H$_2$) in a stoichiometry of 1:1:1 as per the consumption. The reaction was conducted in a 300 ml Stainless Steel reactor as follows: aqueous phase—(35%) formaldehyde—30 cm$^3$, water—50 cm$^3$' diethyl amine—1.86×10$^{-2}$ moles, acetic—1.76×10$^2$ moles; organic phase: Toluene—20 cm$^3$, HRh (CO)PPh$_3$)$_3$—5.44×10$^{-5}$ moles, PPh$_3$—3.66×10$^{-4}$ moles the a was pressurized with syngas 3.772 Mpa, (CO: H$_2$, 1:1) and ethylene 0.419 MPa. The autoclave was heated up to 333 K, the only difference being that ethylene, and syngas (CO/H$_2$) in a stoichiometry of 1:1:1 as per the consumption were supplied to the reactor, which was maintained at a constant pressure. The reaction was carried out for 7 hours. A total of 0.04 mol of ethylene and 0.04 mol of carbon monoxide and hydrogen each were fed to the reactor, during this period, to make up for the drop in pressure due to the consumption of ethylene, carbon monoxide and hydrogen in the required stoichiometry. At the end of 7 hours the reactor was cooled and the contents analysed. The methacrolein formed was 0.0375 mol along with propionaldehyde 0.0021 mol. This corresponds to a selectivity of 93.8% to methacrolein based on ethylene conversion.

EXAMPLE 9

Example 9 shows the activity of the catalysts system on recycle. A reaction was taken in a 300 ml Stainless steel reactor as follows: aqueous phase (35%) formaldehyde—30 cm$^3$, water—50 cm$^3$, diethyl amine—1.86×10$^{-2}$ moles, acetic acid—1.76×10$^{-2}$ moles. Organic phase: Toluene—20 cm$^3$, HRh(CO)(PPH$_3$)$_3$—5.44×10$^{-5}$ moles PPh$^3$—3.66×10$^{-4}$ moles. The autoclave was pressurized with syngas 3.772 Mpa, (CO:H$_2$, 1:1) and ethylene 0.419 Mpa. The autoclave was heated up to 333 K and the reaction was continued for 6 hours. At the end of the reaction the autoclave and its contents were cooled to room temperature. The analysis of the product showed 67% conversion of ethylene with propionaldehyde 0.0035 mol and methacrolein 0.234 mol. Following this the organic phase of the reaction was vacuum distilled to remove methacrolein and made up to 20 ml with toluene, to make up for the loss of toluene during distillation. This organic phase was recycled to the reactor along with the aqueous phase and the reaction was taken under the conditions mentioned earlier. At the end of 6 hours the reactor was discharged. The analysis of the product showed 74% conversion of ethylene with propionaldehyde 0.00207 mol and methacrolein 0.0198 mol.

From these examples it is clear that when the reaction is carried out in a way such that both catalysts are present in the same phase i.e. either aqueous or organic phase, the interaction between the two, under reaction conditions results in the deactivation of the aldolisation catalyst. Hence a segregation of the two catalysts is essential to achieve a stable and robust catalytic system capable of catalyzing the tandem reaction of hydroformylation and aldolisatin respectively. This has been achieved by solubilising the hydroformylation catalyst in the organic phase, wherein the olefin and syngas have a high solubility, so as to have the hydroformlation reaction in high efficiency. The product formed has reasonable solubility in the aqueous phase where the aldolisation catalyst is localized, along with the formaldehyde that is highly soluble in water formaldehyde rich medium resulting in cross aldol formation as against the homo aldol formation. The acrolein products formed are more soluble in the organic phase and hence removed from the aqueous phase, avoiding degradation due to the aqueous phase catalyst.

The main advantage of the present invention are:
1. A strategy for the segregation of two non compatible catalysts into two distinct phases, to result in an active catalyst combination to facilitate a tandem sequential reaction using the two catalysts, in their respective media. This approach is demonstrated for the tandem synthesis of α-substituted acroleins.
2. A direct one-pot preparation of α-substituted acroleins from olefin by hydroformylation reaction followed by aldol condensation of the formed aldehydes with formaldehyde already present in the reactor.
3. in this process both the reaction i.e. hydroformylation and aldol condensation are conducted simultaneously in a biphasic aqueous-organic system, such that the catalyst for the hydroformylation reaction is present in the organic medium. And the aldol catalyst is present in the aqueous medium. This compartmentalization of two catalysts avoid the direct contact of the two catalyst which otherwise leads to deactivation of the aldol catalyst.
4. This one process is distinctly advantageous over hitherto known processes wherein the hydroformylation and aldol condensation is done in two stages.
5. Since the aldol condensation with formaldehyde takes place in water which contains formaldehyde, cross aldol formation is favored over home aldol formation leading to a high selectivity over conventional methods.

We claim:

1. A process for preparing an α-substituted acrolein having the formula CH2=CR—CHO, wherein R is an alkyl group or an aryl group, comprising:
  (i) subjecting a mixture of an olefin and syngas or a mixture of an olefin, carbon monoxide and hydrogen to hydroformylation in an organic phase in the presence of a hydroformylation catalyst or catalyst precursor that is a rhodium complex catalyst or catalyst precursor to obtain the corresponding aldehyde; and
  (ii) subjecting the aldehyde obtained in step (i) to aldol condensation with formaldehyde in an aqueous phase in the presence of an aldolisation catalyst that is a secondary amine or a secondary amine/organic acid catalyst,
  wherein reactions (i) and (ii) are carried out simultaneously in a biphasic aqueous-organic system, and the hydroformylation catalyst and the aldolisation catalyst are segregated in the two phases.

2. The process of claim 1, wherein the rhodium complex catalyst has the formula $Rh(A)_p(B)_q(C)_r(D)_s$, wherein A, B, C and D are each independently selected from the group consisting of H, a trialkyl phosphine, a triaryl phosphine, carbonyl, a trialkyl arsine, a triaryl arsine, an alkylaryl phosphine, a trialkyl amine, a triaryl amine, an alkylaryl amine, a bisphosphine and a diimine, the sum of p and q and r and s is equal to 4, 5, or 6, and the catalyst is soluble in the organic phase.

3. The process of claim 1 wherein the organic phase is selected from the group consisting of an aromatic hydrocarbon, an aliphatic hydrocarbon, a higher alcohol, and mixtures thereof.

4. The process of claim 1 wherein the rhodium complex catalyst is selected from the group consisting of $HRh(CO)(PPH_3)_3$, $Rh(CO)(Cl)(PPh_3)_2$, $HRh(CO)_2$(acetylacetone), $[Rh(Cyclooctadiene)Cl]_2$, $HRh(CO)(P(n-butyl)_3)_3$, $HRh(CO)(PPh_3)$(diphenylphosphinoethane), $HRh(CO)(PPh_3)$(diphenylphosphinopropane), and $HRh(CO)(PPh_3$(diphenylphosphinobutane).

5. The process of claim 1 wherein reaction (i) is carried out in the presence of a rhodium catalyst precursor having an additional coordinated ligand and an additional free ligand that is not coordinated to the rhodium metal, wherein the additional free ligand is identical to or different from the additional coordinated ligand.

6. The process of claim 5 wherein the additional coordinated ligand and the additional free ligand are water insoluble and are each independently selected from the group consisting of an aryl secondary phosphine, an alkyl secondary phosphine, an alkylaryl secondary phosphine, an aryl tertiary phosphine, an alkyl tertiary phosphine, an alkylaryl tertiary phosphine, an aryl secondary phosphate, an alkyl secondary phosphate, an alkylaryl secondary phosphate, an aryl tertiary phosphate, an alkyl tertiary phosphate, an alkylaryl tertiary phosphate, an aryl secondary arsine, an alkyl secondary arsine, an alkylaryl secondary arsine, an aryl tertiary arsine, an alkyl tertiary arsine, an alkylaryl tertiary arsine, an aryl tertiary amine, an alkyl tertiary amine, an alkylaryl tertiary amine, a pentanedione, a substituted pentanedione, an acetylacetonate, a Schiff base, an aryl bisphosphine, an alkyl bisphosphine, and an alkylaryl bisphosphine.

7. The process of claim 6 wherein the additional coordinated ligand and the additional free ligand are each independently selected from the group consisting of triphenylphosphine, tri n-butylphosphine, acetylacetone, tributylphosphite, triphenylphosphite, triphenylamine, tributylamine and triphenylarsine.

8. The process of claim 5 wherein reaction (i) is carried out in presence of excess free ligand and a mole ratio of rhodium metal to free ligand in the range of 0.1 to 10.

9. The process of claim 1 wherein the aldolisation catalyst is soluble in the aqueous phase and is a secondary aryl or alkyl amine selected from the group consisting of diethyl amine, dimethyl amine, methyl ethyl amine, dibutyl amine, dibenzyl diphenyl amine, piperidine, morpholine, piperazine and pyrrolidine.

10. The process of claim 1 wherein the aldolisation catalyst is a secondary amine/organic acid catalyst and the organic acid is selected from the group consisting of acetic acid, propionic acid and butyric acid.

11. The process of claim 10 wherein the mole ratio of the secondary amine to the organic acid is in the range of 0.01 to 10.

12. The process of claim 1 wherein the mole ratio of the hydroformylation catalyst to the aldolisation catalyst is in the range of 0.01 to 10,000.

13. The process of claim 12 wherein the mole ratio of the hydroformylation catalyst to the aldolisation catalyst is in the range of 0.1 to 1,000.

14. The process of claim 1 wherein the organic phase is immiscible with water and is selected from the group consisting of toluene, xylene, cyclohexane, heptane, decanol and a mixture thereof.

15. The process of claim 1 wherein the formaldehyde is in the form of an aqueous solution or paraformaldehyde.

16. The process of claim 1 wherein the mole ratio of olefin to formaldehyde is in the range of 0.1 to 100.

17. The process of claim 16 wherein the mole ratio of olefin to formaldehyde is in the range of 0.5 to 10.

18. The process of claim 1 wherein the olefin is a substituted or unsubstituted olefin having from 2 to 10 carbon atoms.

19. The process of claim 1 wherein reactions (i) and (ii) are carried out at a temperature between 20° C. and 200° C.

20. The process of claim 1 wherein the pressures of carbon monoxide and hydrogen are each independently in the range of 10 to 1500 psi.

21. The process of claim 20 wherein the pressures of carbon monoxide and hydrogen are each independently in the range of 50 to 450 psi.

22. The process of claim 1 wherein the $\alpha$ substituted acrolein product is preferentially soluble in the organic phase.

23. The process of claim 1 wherein reactions (i) and (ii) are conducted either as a batch or as a continuous reaction wherein the olefin, carbon monoxide, and hydrogen are added continuously at a rate that is dependent on their rate of consumption.

24. The process of claim 1 wherein the olefin is ethylene and the $\alpha$-substituted acrolein is methacrolein.

* * * * *